US009809507B2

(12) United States Patent
Yanagawa et al.

(10) Patent No.: US 9,809,507 B2
(45) Date of Patent: *Nov. 7, 2017

(54) CATALYST FOR PRODUCING MONOCYCLIC AROMATIC HYDROCARBONS, AND METHOD FOR PRODUCING MONOCYCLIC AROMATIC HYDROCARBONS

(71) Applicant: JX Nippon Oil & Energy Corporation, Tokyo (JP)

(72) Inventors: Shinichiro Yanagawa, Tokyo (JP); Masahide Kobayashi, Tokyo (JP); Yuko Aoki, Tokyo (JP); Kazuaki Hayasaka, Tokyo (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 374 days.

This patent is subject to a terminal disclaimer.

(21) Appl. No.: 14/467,707

(22) Filed: Aug. 25, 2014

(65) Prior Publication Data

US 2014/0364667 A1    Dec. 11, 2014

Related U.S. Application Data

(62) Division of application No. 13/138,082, filed as application No. PCT/JP2010/002171 on Mar. 26, 2010, now abandoned.

(30) Foreign Application Priority Data

Jun. 30, 2009  (JP) ................................. 2009-155984

(51) Int. Cl.
| | |
|---|---|
| C07C 4/06 | (2006.01) |
| B01J 29/06 | (2006.01) |
| B01J 29/40 | (2006.01) |
| C10G 45/68 | (2006.01) |
| B01J 37/28 | (2006.01) |

(52) U.S. Cl.
CPC .............. *C07C 4/06* (2013.01); *B01J 29/061* (2013.01); *B01J 29/405* (2013.01); *C10G 45/68* (2013.01); *B01J 37/28* (2013.01); *B01J 2229/37* (2013.01); *C07C 2529/06* (2013.01); *C07C 2529/40* (2013.01); *C07C 2529/87* (2013.01); *C10G 2300/1033* (2013.01); *C10G 2300/1044* (2013.01); *C10G 2300/1048* (2013.01); *C10G 2300/1051* (2013.01); *C10G 2300/1055* (2013.01); *C10G 2300/1059* (2013.01); *C10G 2300/301* (2013.01); *C10G 2400/30* (2013.01)

(58) Field of Classification Search
USPC ........................................................ 585/476
See application file for complete search history.

(56) References Cited

U.S. PATENT DOCUMENTS

| | | | |
|---|---|---|---|
| 4,394,300 | A | 7/1983 | Chu et al. |
| 4,585,545 | A | 4/1986 | Yancey, Jr. et al. |
| 5,770,047 | A | 6/1998 | Salazar et al. |
| 5,898,089 | A | 4/1999 | Drake et al. |
| 6,255,243 | B1 | 7/2001 | Drake et al. |
| 6,617,275 | B1 | 9/2003 | Sharma et al. |
| 2001/0056217 | A1 | 12/2001 | Froment et al. |
| 2007/0293714 | A1 | 12/2007 | Long et al. |
| 2009/0314683 | A1 | 12/2009 | Matsushita |

FOREIGN PATENT DOCUMENTS

| | | |
|---|---|---|
| EP | 2050731 | 4/2009 |
| JP | 60-19726 | 1/1985 |
| JP | 03-002128 | 1/1991 |
| JP | 03-026791 | 2/1991 |
| JP | 03-52993 | 3/1991 |
| JP | 10-60457 | 3/1998 |
| JP | 2001-525725 | 12/2001 |
| JP | 2002-525380 | 8/2002 |
| JP | 2007-190520 | 8/2007 |
| JP | 2007-530266 | 11/2007 |

(Continued)

OTHER PUBLICATIONS

Office Action dated Jul. 18, 2014 issued in Chinese Application No. 201080028411.1 [with English Translation].

(Continued)

Primary Examiner — Elizabeth Wood
(74) Attorney, Agent, or Firm — Andrews Kurth Kenyon LLP

(57) ABSTRACT

A catalyst for producing monocyclic aromatic hydrocarbons of 6 to 8 carbon number from a feedstock oil having a 10 volume % distillation temperature of at least 140° C. and an end point temperature of not more than 400° C., or a feedstock oil having a 10 volume % distillation temperature of at least 140° C. and a 90 volume % distillation temperature of not more than 360° C., wherein the catalyst contains a crystalline aluminosilicate, gallium and/or zinc, and phosphorus, and the amount of phosphorus supported on the crystalline aluminosilicate is within a range from 0.1 to 1.9% by mass based on the mass of the crystalline aluminosilicate; and a method for producing monocyclic aromatic hydrocarbons, the method involving bringing a feedstock oil having a 10 volume % distillation temperature of at least 140° C. and an end point temperature of not more than 400° C., or a feedstock oil having a 10 volume % distillation temperature of at least 140° C. and a 90 volume % distillation temperature of not more than 360° C., into contact with the above-mentioned catalyst for producing monocyclic aromatic hydrocarbons.

10 Claims, No Drawings

(56) References Cited

FOREIGN PATENT DOCUMENTS

| KR | 10-2001-0012397 | 2/2001 |
|---|---|---|
| WO | WO 98/51409 | 11/1998 |
| WO | WO 00/18853 | 4/2000 |
| WO | WO 2007/135769 | 11/2007 |
| WO | 2010/109897 A1 | 9/2010 |
| WO | 2011/090121 A1 | 7/2011 |

OTHER PUBLICATIONS

International Search Report dated Jun. 29, 2010 issued in corresponding PCT Application No. PCT/JP2010/002171.

Chinese Office Action dated May 20, 2013, issued in corresponding Chinese Application No. 201080028411.1.

European Search Report dated Jul. 24, 2013 issued in corresponding EP Application No. 10 79 3750.

International Search Report dated Jun. 29, 2010 issued in related PCT Application No. PCT/JP2010/002227.

Office Action dated Apr. 18, 2013 issued in U.S. Appl. No. 13/138,065.

Office Action dated May 24, 2013 issued in related CN Application No. 201080032470.6.

Search Report dated Jul. 23, 2013 issued in related EP Application No. 10804025.4.

Office Action dated Aug. 28, 2013 issued in U.S. Appl. No. 13/138,065.

International Search Report dated Mar. 6, 2012 in a corresponding PCT application No. PCT/JP2011/080417.

European Search Report dated Jul. 21, 2014 in a corresponding EP application No. 11853615.0.

Office Action dated Dec. 9, 2015 in corresponding Korean Application No. 10-2012-7002908.

Chun Yang, et al., "Boronation and galliation of zeolite β in an alkaline medium", Materials Chemistry and Physics, vol. 53, pp. 55-66(2000).

CATALYST FOR PRODUCING MONOCYCLIC AROMATIC HYDROCARBONS, AND METHOD FOR PRODUCING MONOCYCLIC AROMATIC HYDROCARBONS

This application is a divisional application of U.S. application Ser. No. 13/138,082, which is a national stage application of International Application No. PCT/JP2010/002171, filed Mar. 26, 2010, which claims priority to Japanese Application No. 2009-155984, filed Jun. 30, 2009, each of which is incorporated by reference in its entirety.

TECHNICAL FIELD

The present invention relates to a catalyst for producing monocyclic aromatic hydrocarbons and a method for producing monocyclic aromatic hydrocarbons that enable the production of monocyclic aromatic hydrocarbons from an oil containing a large amount of polycyclic aromatic hydrocarbons.

Priority is claimed on Japanese Patent Application No. 2009-155984, filed Jun. 30, 2009, the content of which is incorporated herein by reference.

BACKGROUND ART

Light cycle oil (hereinafter also referred to as LCO), which is a cracked gas oil produced in a fluid catalytic cracking, contains a large amount of polycyclic aromatic hydrocarbons, and has been used as a gas oil or a heating oil. However, in recent years, investigations have been conducted into the possibilities of obtaining, from LCO, monocyclic aromatic hydrocarbons of 6 to 8 carbon number (such as benzene, toluene, xylene and ethylbenzene), which can be used as high-octane gasoline base stocks or petrochemical feedstocks, and offer significant added value.

For example, Patent Documents 1 to 3 propose methods that use zeolite catalysts to produce monocyclic aromatic hydrocarbons from the polycyclic aromatic hydrocarbons contained in large amounts within LCO and the like.

However, in the methods disclosed in Patent Documents 1 to 3, the yields of monocyclic aromatic hydrocarbons of 6 to 8 carbon number were not entirely satisfactory.

When monocyclic aromatic hydrocarbons are produced from a heavy feedstock oil containing polycyclic aromatic hydrocarbons, large amounts of carbon matter are deposited on the catalyst, causing a rapid deterioration in the catalytic activity, and therefore a catalyst regeneration process that removes this carbon matter must be performed frequently. Further, in those cases where a circulating fluidized bed is employed, which is a process in which the reaction and catalyst regeneration are repeated in an efficient manner, the temperature for the catalyst regeneration must be set to a higher temperature than the reaction temperature, resulting in a particularly severe temperature environment for the catalyst.

Under these types of severe conditions, if a zeolite catalyst is used as the catalyst, then the catalyst tends to suffer from hydrothermal degradation, causing a deterioration in the reaction activity over time, and therefore improvements in the hydrothermal stability of the catalyst are required. However, the zeolite catalysts disclosed in Patent Documents 1 to 3 employ no measures to improve the hydrothermal stability, and offer very little practical usability.

Examples of known methods for improving the hydrothermal stability include a method that uses a zeolite having a high Si/Al ratio, a method in which the catalyst is subjected to a preliminary hydrothermal treatment to stabilize the catalyst, such as USY zeolite, a method in which phosphorus is added to a zeolite, a method in which a rare earth metal is added to a zeolite, and a method that involves improving the structure-directing agent used during the synthesis of a zeolite.

Of these methods, the addition of phosphorus not only improves the hydrothermal stability, but also provides other known effects such as an improvement in selectivity due to suppression of carbon matter deposition during fluid catalytic cracking, and an improvement in the abrasion resistance of the binder. Accordingly, this method is frequently applied to catalysts used in catalytic cracking reactions.

Examples of catalytic cracking catalysts prepared by adding phosphorus to a zeolite include those disclosed in Patent Documents 4 to 6.

Namely, Patent Document 4 discloses a method for producing olefins from naphtha using a catalyst containing ZSM-5 to which has been added phosphorus, as well as gallium, germanium and/or tin. In Patent Document 4, phosphorus is added for the purposes of suppressing the production of methane and aromatics in order to enhance the selectivity for olefin production, and ensuring a high degree of activity even for a short contact time, thereby improving the yield of olefins.

Patent Document 5 discloses a method for producing olefins in a high yield from heavy hydrocarbons by using a catalyst prepared by supporting phosphorus on ZSM-5 containing zirconium and a rare earth element, and a catalyst containing a USY zeolite, an REY zeolite, kaolin, silica and alumina.

Patent Document 6 discloses a method for producing ethylene and propylene in a high yield by transforming hydrocarbons using a catalyst containing ZSM-5 having phosphorus and a transition metal element supported thereon.

As mentioned above, the addition of phosphorus to zeolites has been disclosed in Patent Documents 4 to 6, but in each of these documents, the main purpose was improvement of the olefin yield, and monocyclic aromatic hydrocarbons of 6 to 8 carbon number were not able to be produced at high yield. For example, Table 2 in Patent Document 6 discloses the yields for olefins (ethylene and propylene) and BTX (benzene, toluene and xylene), and whereas the yield for the olefins was 40% by mass, the yield for BTX was a low value of approximately 6% by mass.

Accordingly, a catalyst for producing monocyclic aromatic hydrocarbons that is capable of producing monocyclic aromatic hydrocarbons of 6 to 8 carbon number in a high yield from a feedstock oil containing polycyclic aromatic hydrocarbons, and also capable of preventing any deterioration over time in the yield of the monocyclic aromatic hydrocarbons is currently not known.

DOCUMENTS OF RELATED ART

Patent Document

[Patent Document 1]
Japanese Unexamined Patent Application, First Publication No. Hei 3-2128
[Patent Document 2]
Japanese Unexamined Patent Application, First Publication No. Hei 3-52993

[Patent Document 3]
Japanese Unexamined Patent Application, First Publication No. Hei 3-26791
[Patent Document 4]
Published Japanese Translation No. 2002-525380 of PCT
[Patent Document 5]
Japanese Unexamined Patent Application, First Publication No. 2007-190520
[Patent Document 6]
Published Japanese Translation No. 2007-530266 of PCT

SUMMARY OF INVENTION

Problems to be Solved by the Invention

An object of the present invention is to provide a catalyst for producing monocyclic aromatic hydrocarbons and a method for producing monocyclic aromatic hydrocarbons that enable the production of monocyclic aromatic hydrocarbons of 6 to 8 carbon number in a high yield from a feedstock oil containing polycyclic aromatic hydrocarbons, and also enable the prevention of any deterioration over time in the yield of the monocyclic aromatic hydrocarbons of 6 to 8 carbon number.

Means to Solve the Problems

[1] A catalyst for producing monocyclic aromatic hydrocarbons, used for producing monocyclic aromatic hydrocarbons of 6 to 8 carbon number from a feedstock oil having a 10 volume % distillation temperature of at least 140° C. and an end point temperature of not more than 400° C., or a feedstock oil having a 10 volume % distillation temperature of at least 140° C. and a 90 volume % distillation temperature of not more than 360° C., wherein
the catalyst contains a crystalline aluminosilicate, gallium and/or zinc, and phosphorus, and the amount of phosphorus supported on the crystalline aluminosilicate is within a range from 0.1 to 1.9% by mass based on the mass of the crystalline aluminosilicate.
[2] A catalyst for producing monocyclic aromatic hydrocarbons, used for producing monocyclic aromatic hydrocarbons of 6 to 8 carbon number from a feedstock oil having a 10 volume % distillation temperature of at least 140° C. and an end point temperature of not more than 400° C., or a feedstock oil having a 10 volume % distillation temperature of at least 140° C. and a 90 volume % distillation temperature of not more than 360° C., wherein
the catalyst contains a crystalline aluminosilicate, gallium and/or zinc, and phosphorus, and the amount of phosphorus is within a range from 0.1 to 5.0% by mass based on the mass of the catalyst.
[3] The catalyst for producing monocyclic aromatic hydrocarbons according to [1] or [2], wherein the crystalline aluminosilicate is a pentasil-type zeolite.
[4] The catalyst for producing monocyclic aromatic hydrocarbons according to any one of [1] to [3], wherein the crystalline aluminosilicate is an MFI-type zeolite.
[5] A method for producing monocyclic aromatic hydrocarbons of 6 to 8 carbon number, the method including bringing a feedstock oil having a 10 volume % distillation temperature of at least 140° C. and an end point temperature of not more than 400° C., or a feedstock oil having a 10 volume % distillation temperature of at least 140° C. and a 90 volume % distillation temperature of not more than 360° C., into contact with the catalyst for producing monocyclic aromatic hydrocarbons according to any one of [1] to [4].
[6] The method for producing monocyclic aromatic hydrocarbons of 6 to 8 carbon number according to [5], wherein a cracked gas oil produced in a fluid catalytic cracking is used as the feedstock oil.
[7] The method for producing monocyclic aromatic hydrocarbons of 6 to 8 carbon number according to [5] or [6], wherein the feedstock oil is brought into contact with the catalyst for producing monocyclic aromatic hydrocarbons in a fluidized bed reactor.

Effect of the Invention

The catalyst for producing monocyclic aromatic hydrocarbons and the method for producing monocyclic aromatic hydrocarbons of 6 to 8 carbon number according to the present invention enable the production of monocyclic aromatic hydrocarbons of 6 to 8 carbon number in a high yield from a feedstock oil containing polycyclic aromatic hydrocarbons, and also enable the prevention of any deterioration over time in the yield of the monocyclic aromatic hydrocarbons of 6 to 8 carbon number.

DESCRIPTION OF EMBODIMENTS (Catalyst for Producing Monocyclic Aromatic Hydrocarbons)

The catalyst for producing monocyclic aromatic hydrocarbons according to the present invention (hereinafter often referred to as "the catalyst") is used for producing monocyclic aromatic hydrocarbons of 6 to 8 carbon number (hereinafter often abbreviated as "monocyclic aromatic hydrocarbons") from a feedstock oil containing polycyclic aromatic hydrocarbons and saturated hydrocarbons, and contains a crystalline aluminosilicate, gallium and phosphorus.

[Crystalline Aluminosilicate]

Although there are no particular limitations on the crystalline aluminosilicate, medium pore size zeolites such as zeolites with MFI, MEL, TON, MTT, MRE, FER, AEL and EUO type crystal structures are preferred, and in terms of maximizing the yield of monocyclic aromatic hydrocarbons, pentasil-type zeolites are more preferred, and zeolites with MFI-type and/or MEL-type crystal structures are particularly desirable.

MFI-type and MEL-type zeolites are included within the conventional zeolite structures published by The Structure Commission of the International Zeolite Association (Atlas of Zeolite Structure Types, W. M. Meiyer and D. H. Olson (1978), distributed by Polycrystal Book Service, Pittsburgh, Pa. (USA)).

The amount of the crystalline aluminosilicate within the catalyst, relative to a value of 100% for the entire catalyst, is preferably within a range from 10 to 95% by mass, more preferably from 20 to 80% by mass, and still more preferably from 25 to 70% by mass. Provided the amount of the crystalline aluminosilicate is not less than 10% by mass and not more than 95% by mass, a satisfactorily high level of catalytic activity can be achieved.

[Gallium]

Examples of the form of the gallium contained within the catalyst of the present invention include catalysts in which the gallium is incorporated within the lattice framework of the crystalline aluminosilicate (crystalline aluminogallosilicates), catalysts in which gallium is supported on the crystalline aluminosilicate (gallium-supporting crystalline aluminosilicates), and catalysts including both of these forms.

A crystalline aluminogallosilicate has a structure in which $SiO_4$, $AlO_4$ and $GaO_4$ structures adopt tetrahedral coordination within the framework. A crystalline aluminogallosilicate can be obtained, for example, by gel crystallization via hydrothermal synthesis, by a method in which gallium is inserted into the lattice framework of a crystalline aluminosilicate, or by a method in which aluminum is inserted into the lattice framework of a crystalline gallosilicate.

A gallium-supporting crystalline aluminosilicate can obtained by supporting gallium on a crystalline aluminosilicate using a conventional method such as an ion-exchange method or impregnation method. There are no particular limitations on the gallium source used in these methods, and examples include gallium salts such as gallium nitrate and gallium chloride, and gallium oxide.

The amount of gallium within the catalyst of the present invention, relative to a value of 100% for the total mass of the crystalline aluminosilicate, is preferably within a range from 0.01 to 5.0% by mass.

[Zinc]

Examples of the form of the zinc contained within the catalyst of the present invention include catalysts in which the zinc is incorporated within the lattice framework of the crystalline aluminosilicate (crystalline aluminozincosilicates), catalysts in which zinc is supported on the crystalline aluminosilicate (zinc-supporting crystalline aluminosilicates), and catalysts including both of these forms.

A crystalline aluminozincosilicate has a structure in which $SiO_4$, $AlO_4$ and $ZnO_4$ structures exist within the framework. A crystalline aluminozincosilicate can be obtained, for example, by gel crystallization via hydrothermal synthesis, by a method in which zinc is inserted into the lattice framework of a crystalline aluminosilicate, or by a method in which aluminum is inserted into the lattice framework of a crystalline zincosilicate.

A zinc-supporting crystalline aluminosilicate can obtained by supporting zinc on a crystalline aluminosilicate using a conventional method such as an ion-exchange method or impregnation method. There are no particular limitations on the zinc source used in these methods, and examples include zinc salts such as zinc nitrate and zinc chloride, and zinc oxide.

The amount of zinc within the catalyst of the present invention, relative to a value of 100% for the total mass of the crystalline aluminosilicate, is preferably within a range from 0.01 to 5.0% by mass.

The catalyst of the present invention may be a catalyst that contains either one of gallium or zinc, or a catalyst that contains both gallium and zinc. Further, the catalyst may also contain one or more other metals in addition to the gallium and/or zinc.

[Phosphorus]

The amount of phosphorus supported on the crystalline aluminosilicate in the catalyst of the present invention, relative to a value of 100% for the total mass of the crystalline aluminosilicate, is preferably within a range from 0.1 to 1.9% by mass. Moreover, the lower limit for this range is more preferably at least 0.2% by mass, whereas the upper limit is more preferably not more than 1.5% by mass, and still more preferably not more than 1.2% by mass. By ensuring that the amount of phosphorus supported on the crystalline aluminosilicate is at least 0.1% by mass, deterioration over time in the yield of the monocyclic aromatic hydrocarbons can be prevented, whereas ensuring that the amount is not more than 1.9% by mass enables the yield of the monocyclic aromatic hydrocarbons to be increased.

The upper limit for the amount of phosphorus within the catalyst of the present invention is considerably lower than the upper limit for the amount of phosphorus within the catalysts disclosed in Patent Documents 4 to 6. It is thought that one reason for this difference is the fact that the feedstock oil for the reaction in which the catalyst of the present invention is used contains a large amount of polycyclic aromatic hydrocarbons and exhibits relatively low reactivity. If the amount of phosphorus is increased too much, then the feedstock oil is even less likely to undergo reaction and the aromatic activity decreases, resulting in a deterioration in the yield of the monocyclic aromatic hydrocarbons. In contrast, the feedstock oils in Patent Documents 4 to 6 (such as a vacuum gas oil used as the feedstock oil for a fluid catalytic cracking) are heavy, have large molecular weights and are adsorbed readily onto the catalyst, and are therefore cracked more readily than fractions such as LCO. Moreover, because cracking to form light olefins is relatively easy, even if a large amount of phosphorus is supported on the catalyst and the aromatic activity decreases to some extent, this does not cause significant problems.

There are no particular limitations on the method used for incorporating the phosphorus within the catalyst of the present invention, and examples include methods in which an ion-exchange method or impregnation method or the like is used to incorporate a phosphorus compound within a crystalline aluminosilicate, crystalline aluminogallosilicate or crystalline aluminozincosilicate, thereby substituting a portion of the framework of the crystalline aluminosilicate with phosphorus, and methods in which a crystallization promoter containing phosphorus is used during synthesis of the zeolite. Although there are no particular limitations on the phosphate ion-containing aqueous solution used during the above method, a solution prepared by dissolving phosphoric acid, diammonium hydrogen phosphate, ammonium dihydrogen phosphate or another water-soluble phosphate salt in water at an arbitrary concentration can be used particularly favorably.

The catalyst of the present invention can be obtained by calcining (at a calcination temperature of 300 to 900° C.) an above-mentioned phosphorus-supporting crystalline aluminogallosilicate or crystalline aluminozincosilicate, or a crystalline aluminosilicate having gallium/zinc and phosphorus supported thereon.

[Form]

The catalyst of the present invention is used in the form of a powder, granules or pellets or the like, depending on the reaction format. For example, a powder is used in the case of a fluidized bed, whereas granules or pellets are used in the case of a fixed bed. The average particle size of the catalyst used in a fluidized bed is preferably within a range from 30 to 180 μm, and more preferably from 50 to 100 μm. Further, the bulk density of the catalyst used in a fluidized bed is preferably within a range from 0.4 to 1.8 g/cc, and more preferably from 0.5 to 1.0 g/cc.

The average particle size describes the particle size at which the particle size distribution obtained by classification using sieves reaches 50% by mass, whereas the bulk density refers to the value measured using the method prescribed in JIS R 9301-2-3.

In order to obtain a catalyst in granular or pellet form, if necessary, an inert oxide may be added to the crystalline aluminosilicate or catalyst as a binder or the like, with the resulting mixture then molded using any of various molding apparatus.

In those cases where the catalyst of the present invention contains an inorganic oxide such as a binder, a compound that contains phosphorus may also be used as the binder.

Further, in those cases where the catalyst contains an inorganic oxide such as a binder, the catalyst may be produced by mixing the binder and the crystalline aluminosilicate, and subsequently adding the gallium and/or zinc and the phosphorus, or by mixing the binder and the gallium- and/or zinc-supporting crystalline aluminosilicate, or mixing the binder and the crystalline aluminogallosilicate and/or crystalline aluminozincosilicate, and subsequently adding the phosphorus.

In those cases where the catalyst contains an inorganic oxide such as a binder, the amount of phosphorus relative to the total mass of the catalyst is preferably within a range from 0.1 to 5.0% by mass, and the lower limit for this range is more preferably at least 0.2% by mass, whereas the upper limit is more preferably not more than 3.0% by mass, and still more preferably not more than 2.0% by mass. By ensuring that the amount of phosphorus is at least 0.1% by mass of the total mass of the catalyst, deterioration over time in the yield of the monocyclic aromatic hydrocarbons can be prevented, whereas ensuring that the amount of phosphorus is not more than 5.0% by mass enables the yield of the monocyclic aromatic hydrocarbons to be increased.

(Method for Producing Monocyclic Aromatic Hydrocarbons)

The method for producing monocyclic aromatic hydrocarbons according to the present invention involves bringing a feedstock oil into contact with the above-mentioned catalyst to effect a reaction.

In this reaction, saturated hydrocarbons function as hydrogen donor sources, and a hydrogen transfer reaction from the saturated hydrocarbons is used to convert polycyclic aromatic hydrocarbons into monocyclic aromatic hydrocarbons.

[Feedstock Oil]

The feedstock oil used in the present invention is either an oil having a 10 volume % distillation temperature of at least 140° C. and an end point temperature of not more than 400° C., or an oil having a 10 volume % distillation temperature of at least 140° C. and a 90 volume % distillation temperature of not more than 360° C. With an oil having a 10 volume % distillation temperature of less than 140° C., the reaction involves production of BTX from light compounds, which is unsuitable in the present embodiment, and therefore the 10 volume % distillation temperature is preferably at least 140° C., and more preferably 150° C. or higher. Further, if an oil having an end point temperature exceeding 400° C. is used, then not only is the yield of monocyclic aromatic hydrocarbons low, but the amount of coke deposition on the catalyst also tends to increase, causing a more rapid deterioration in the catalytic activity, and therefore the end point temperature of the feedstock oil is preferably not more than 400° C., and more preferably 380° C. or lower. Furthermore, if a feedstock oil having a 90 volume % distillation temperature that exceeds 360° C. is used, then the amount of coke deposition on the catalyst tends to increase, causing a more rapid deterioration in the catalytic activity, and therefore the 90 volume % distillation temperature for the feedstock oil is preferably not more than 360° C., and more preferably 350° C. or lower.

In this description, the 10 volume % distillation temperature, the 90 volume % distillation temperature and the end point temperature refer to values measured in accordance with the methods prescribed in JIS K2254 "Petroleum products—determination of distillation characteristics".

Examples of feedstock oils having a 10 volume % distillation temperature of at least 140° C. and an end point temperature of not more than 400° C., or feedstock oils having a 10 volume % distillation temperature of at least 140° C. and a 90 volume % distillation temperature of not more than 350° C. include cracked gas oils (LCO) produced in a fluid catalytic cracking, coal liquefaction oil, hydrocracked oil from heavy oils, straight-run kerosene, straight-run gas oil, coker kerosene, coker gas oil, and hydrocracked oil from oil sands. Of these, cracked gas oils (LCO) produced in a fluid catalytic cracking are particularly desirable.

Further, if the feedstock oil contains a large amount of polycyclic aromatic hydrocarbons, then the yield of monocyclic aromatic hydrocarbons of 6 to 8 carbon number tends to decrease, and therefore the amount of polycyclic aromatic hydrocarbons (the polycyclic aromatic content) within the feedstock oil is preferably not more than 50 volume %, and more preferably 30 volume % or less.

In this description, the polycyclic aromatic content describes the combined total of the amount of bicyclic aromatic hydrocarbons (the bicyclic aromatic content) and the amount of tricyclic and higher aromatic hydrocarbons (the tricyclic and higher aromatic content) measured in accordance with JPI-5S-49 "Petroleum Products —Determination of Hydrocarbon Types—High Performance Liquid Chromatography".

[Reaction Format]

Examples of the reaction format used for bringing the feedstock oil into contact with the catalyst for reaction include fixed beds, moving beds and fluidized beds. In the present invention, because a heavy oil fraction is used as the feedstock, a fluidized bed is preferred as it enables the coke fraction adhered to the catalyst to be removed in a continuous manner and enables the reaction to proceed in a stable manner. A continuous regeneration-type fluidized bed, in which the catalyst is circulated between the reactor and a regenerator, thereby continuously repeating a reaction-regeneration cycle, is particularly desirable. The feedstock oil that makes contact with the catalyst is preferably in a gaseous state. Further, the feedstock may be diluted with a gas if required. Furthermore, in those cases where unreacted feedstock occurs, this may be recycled as required.

[Reaction Temperature]

Although there are no particular limitations on the reaction temperature during contact of the feedstock oil with the catalyst for reaction, a reaction temperature of 350 to 700° C. is preferred. In terms of achieving satisfactory reactivity, the lower limit is more preferably 450° C. or higher. On the other hand, an upper limit temperature of not more than 650° C. is preferable as it is not only more advantageous from an energy perspective, but also enables reliable regeneration of the catalyst.

[Reaction Pressure]

The reaction pressure during contact of the feedstock oil with the catalyst for reaction is preferably not more than 1.0 MPaG. Provided the reaction pressure is not more than 1.0 MPaG, the generation of by-product light gases can be prevented, and the pressure resistance required for the reaction apparatus can be lowered.

[Contact Time]

There are no particular limitations on the contact time between the feedstock oil and the catalyst, provided the desired reaction proceeds satisfactorily, but in terms of the gas transit time across the catalyst, a time of 1 to 300 seconds is preferred. The lower limit for this time is more preferably at least 5 seconds, and the upper limit is more preferably 150 seconds or less. Provided the contact time is at least 1 second, a reliable reaction can be achieved, whereas provided the contact time is not more than 300 seconds, deposition of carbon matter on the catalyst due to coking or the like can be suppressed. Further, the amount of light gas generated by cracking can also be suppressed.

In the method for producing monocyclic aromatic hydrocarbons according to the present invention, hydrogen transfer occurs from saturated hydrocarbons to the polycyclic aromatic hydrocarbons, and the polycyclic aromatic hydrocarbons undergo partial hydrogenation and ring opening, yielding monocyclic aromatic hydrocarbons.

In the present invention, the yield of monocyclic aromatic hydrocarbons is preferably at least 15% by mass, more preferably at least 20% by mass, and still more preferably 25% by mass or greater. If the yield of monocyclic aromatic hydrocarbons is less than 15% by mass, then the concentration of the target compounds within the reaction product is low, and the efficiency with which those compounds can be recovered tends to deteriorate.

In the above-mentioned production method of the present invention, because the catalyst described above is used, monocyclic aromatic hydrocarbons can be produced in a high yield, and deterioration over time in the yield of the monocyclic aromatic hydrocarbons can be prevented.

EXAMPLES

The present invention is described in more detail below based on a series of examples and comparative examples, but the present invention is in no way limited by these examples.

Catalyst Preparation Example 1

A solution (A) composed of 1706.1 g of sodium silicate (J Sodium Silicate No. 3, $SiO_2$: 28 to 30% by mass, Na: 9 to 10% by mass, remainder: water, manufactured by Nippon Chemical Industrial Co., Ltd.) and 2227.5 g of water, and a solution (B) composed of 64.2 g of $Al_2(SO_4)_3 \cdot 14\text{~}18H_2O$ (special reagent grade, manufactured by Wako Pure Chemical Industries, Ltd.), 369.2 g of tetrapropylammonium bromide, 152.1 g of $H_2SO_4$ (97% by mass), 326.6 g of NaCl and 2975.7 g of water were prepared independently.

Subsequently, with the solution (A) undergoing continuous stirring at room temperature, the solution (B) was added gradually to the solution (A). The resulting mixture was stirred vigorously for 15 minutes using a mixer, thereby breaking up the gel and forming a uniform fine milky mixture.

This mixture was placed in a stainless steel autoclave, and a crystallization operation was performed under conditions including a temperature of 165° C., a reaction time of 72 hours, a stirring rate of 100 rpm, and under self-generated pressure. Following completion of the crystallization operation, the product was filtered, the solid product was recovered, and an operation of washing the solid product and then performing filtration was repeated 5 times, using a total of approximately 5 liters of deionized water in the 5 times of operations. The solid material obtained upon the final filtration was dried at 120° C., and was then calcined under a stream of air at 550° C. for 3 hours.

Analysis of the resulting calcined product by X-ray diffraction (apparatus model: Rigaku RINT-2500V) confirmed that the product had an MFI structure. Further, X-ray fluorescence analysis (apparatus model: Rigaku ZSX101e) revealed a $SiO_2/Al_2O_3$ ratio (molar ratio) of 64.8. Based on these results, the amount of aluminum element incorporated within the lattice framework was calculated as 1.32% by mass.

A 30% by mass aqueous solution of ammonium nitrate was added to the calcined product in a ratio of 5 mL of the aqueous solution per 1 g of the calcined product, and after heating at 100° C. with constant stirring for 2 hours, the mixture was filtered and washed with water. This operation was performed 4 times in total, and the product was then dried for 3 hours at 120° C., yielding an ammonium-type crystalline aluminosilicate. Subsequently, the product was calcined for 3 hours at 780° C., yielding a proton-type crystalline aluminosilicate.

Next, 120 g of the obtained proton-type crystalline aluminosilicate was impregnated with 120 g of an aqueous solution of gallium nitrate in order to support 0.2% by mass of gallium (based on a value of 100% for the total mass of the crystalline aluminosilicate), and the resulting product was then dried at 120° C. Subsequently, the product was calcined for 3 hours at 780° C. under a stream of air, yielding a gallium-supporting crystalline aluminosilicate.

Subsequently, 30 g of the obtained gallium-supporting crystalline aluminosilicate was impregnated with 30 g of an aqueous solution of diammonium hydrogen phosphate in order to support 0.2% by mass of phosphorus on the aluminosilicate (based on a value of 100% for the total mass of the crystalline aluminosilicate), and the resulting product was then dried at 120° C. Subsequently, the product was calcined for 3 hours at 780° C. under a stream of air, yielding a catalyst containing the crystalline aluminosilicate, gallium and phosphorus.

Tablet molding was performed by applying a pressure of 39.2 MPa (400 kgf) to the obtained catalyst, and the resulting tablets were subjected to coarse crushing and then classified using a 20 to 28 mesh size, thus yielding a granular catalyst 1 (hereinafter referred to as the "granulated catalyst 1").

Catalyst Preparation Example 2

With the exception of impregnating the gallium-supporting crystalline aluminosilicate with 30 g of an aqueous solution of diammonium hydrogen phosphate that had been prepared with a concentration sufficient to support 0.7% by mass of phosphorus on the aluminosilicate (based on a value of 100% for the total mass of the crystalline aluminosilicate), a granular catalyst 2 (hereinafter referred to as the "granulated catalyst 2") was obtained in the same manner as that described in catalyst preparation example 1.

Catalyst Preparation Example 3

With the exception of impregnating the gallium-supporting crystalline aluminosilicate with 30 g of an aqueous solution of diammonium hydrogen phosphate so as to support 1.2% by mass of phosphorus on the aluminosilicate (based on a value of 100% for the total mass of the crystalline aluminosilicate), a granular catalyst 3 (hereinafter referred to as the "granulated catalyst 3") was obtained in the same manner as that described in catalyst preparation example 1.

Catalyst Preparation Example 4

18 g of fumed silica was impregnated with 30 g of an aqueous solution of diammonium hydrogen phosphate so as to incorporate 8.2% by mass of phosphorus within the silica, and the resulting product was dried at 120° C. Subsequently, the product was calcined for 3 hours at 780° C. under a stream of air, yielding a phosphorus-containing fumed silica. 18 g of this phosphorus-containing fumed silica was mixed with 12 g of the catalyst prepared in catalyst preparation example 2, the thus obtained catalyst was subjected to tablet molding by applying a pressure of 39.2 MPa (400 kgf), and the resulting tablets were subjected to coarse crushing and then classified using a 20 to 28 mesh size, thus yielding a granular catalyst 4 (hereinafter referred to as the "granulated catalyst 4").

Catalyst Preparation Example 5

With the exceptions of impregnating 120 g of the proton-type crystalline aluminosilicate with 30 g of an aqueous solution of zinc nitrate hexahydrate that had been prepared with a concentration sufficient to support 0.2% by mass of zinc on the aluminosilicate (based on a value of 100% for the total mass of the crystalline aluminosilicate), thus yielding a zinc-supporting crystalline aluminosilicate, and impregnating the zinc-supporting crystalline aluminosilicate with 30 g of an aqueous solution of diammonium hydrogen phosphate that had been prepared with a concentration sufficient to support 0.7% by mass of phosphorus on the aluminosilicate (based on a value of 100% for the total mass of the crystalline aluminosilicate), a granular catalyst 5 (hereinafter referred to as the "granulated catalyst 5") was obtained in the same manner as that described in catalyst preparation example 1.

Catalyst Preparation Example 6

A mixed solution containing 106 g of sodium silicate (J Sodium Silicate No. 3, $SiO_2$: 28 to 30% by mass, Na: 9 to 10% by mass, remainder: water, manufactured by Nippon Chemical Industrial Co., Ltd.) and pure water was added dropwise to a dilute sulfuric acid solution to prepare a silica sol aqueous solution ($SiO_2$ concentration: 10.2%). Meanwhile, distilled water was added to 20.4 g of the catalyst prepared in catalyst preparation example 2 and containing a crystalline aluminosilicate, gallium and phosphorus to prepare a zeolite slurry. The zeolite slurry was mixed with 300 g of the silica sol aqueous solution, and the resulting slurry was spray dried at 250° C., yielding a spherically shaped catalyst. Subsequently, the catalyst was calcined for 3 hours at 600° C., yielding a powdered catalyst 6 (hereinafter referred to as the "powdered catalyst 6") having an average particle size of 85 μm and a bulk density of 0.75 g/cc.

Catalyst Preparation Example 7

With the exception of impregnating the gallium-supporting crystalline aluminosilicate with 30 g of an aqueous solution of diammonium hydrogen phosphate so as to support 2.0% by mass of phosphorus on the aluminosilicate (based on a value of 100% for the total mass of the crystalline aluminosilicate), a granular catalyst 7 (hereinafter referred to as the "granulated catalyst 7") was obtained in the same manner as that described in catalyst preparation example 1.

Catalyst Preparation Example 8

With the exception of not impregnating the gallium-supporting crystalline aluminosilicate with an aqueous solution of diammonium hydrogen phosphate, a granular catalyst 8 (hereinafter referred to as the "granulated catalyst 8") was obtained in the same manner as that described in catalyst preparation example 1.

The initial reaction catalytic activity and the catalytic activity following hydrothermal degradation of the thus obtained granulated catalysts and powdered catalyst were evaluated using the methods outlined below.

[Evaluation of Initial Reaction Catalytic Activity: Evaluation 1]

Using a circulating reaction apparatus in which the reactor had been charged with a granulated catalyst (10 ml), a feedstock oil having the properties shown in Table 1 was brought into contact with the granulated catalyst and reacted under conditions including a reaction temperature of 550° C. and a reaction pressure of 0 MPaG. During the reaction, nitrogen was introduced as a diluent so that the contact time between the feedstock oil and the granulated catalyst was 7 seconds.

Reaction was continued under these conditions for 30 minutes to produce monocyclic aromatic hydrocarbons of 6 to 8 carbon number, and a compositional analysis of the products was performed using an FID gas chromatograph connected directly to the reaction apparatus in order to evaluate the initial reaction reactivity. The evaluation results are shown in Table 2.

Within the products shown in Table 2, the heavy fraction refers to hydrocarbons of 6 or more carbon number other than the monocyclic aromatic hydrocarbons of 6 to 8 carbon number, the light naphtha refers to hydrocarbons of 5 or 6 carbon number, the liquefied petroleum gas refers to hydrocarbons of 3 or 4 carbon number, and the cracked gas refers to hydrocarbons of not more than 2 carbon number.

[Measurement of Yield of Monocyclic Aromatic Hydrocarbons in Initial Reaction: Evaluation 2]

Using a circulating reaction apparatus in which the reactor had been charged with a powdered catalyst (400 g), a feedstock oil having the properties shown in Table 1 was brought into contact with the powdered catalyst and reacted under conditions including a reaction temperature of 550° C. and a reaction pressure of 0.1 MPaG. For the reaction, the powdered catalyst was packed in a reaction tube with a diameter of 60 mm. During the reaction, nitrogen was introduced as a diluent so that the contact time between the feedstock oil and the powdered catalyst was 10 seconds.

Reaction was continued under these conditions for 10 minutes to produce monocyclic aromatic hydrocarbons of 6 to 8 carbon number, and a compositional analysis of the products was performed using an FID gas chromatograph connected directly to the reaction apparatus in order to evaluate the initial reaction reactivity. The evaluation results are shown in Table 2.

Within the products shown in Table 2, the heavy fraction refers to hydrocarbons of 6 or more carbon number other than the monocyclic aromatic hydrocarbons of 6 to 8 carbon number, the light naphtha refers to hydrocarbons of 5 or 6 carbon number, the liquefied petroleum gas refers to hydrocarbons of 3 or 4 carbon number, and the cracked gas refers to hydrocarbons of not more than 2 carbon number.

[Evaluation of Catalytic Activity Following Hydrothermal Degradation: Evaluation 3]

The granulated catalysts 1 to 5 and 8 and the powdered catalyst 6 were each subjected to a hydrothermal treatment under conditions including a treatment temperature of 650° C. and a treatment time of 6 hours in a 100% by mass steam atmosphere, thus preparing pseudo-degraded catalysts 1 to 6 and 8 that had undergone a simulated hydrothermal degradation.

With the exception of using these pseudo-degraded catalysts 1 to 5 and 8 instead of the granulated catalysts 1 to 5 and 8, the same process as that described for evaluation 1 was used to react the feedstock oil and then perform a compositional analysis of the resulting products to evaluate the catalytic activity following hydrothermal degradation. The evaluation results are shown in Table 2.

Further, with the exception of using the pseudo-degraded catalyst 6 instead of the powdered catalyst 6, the same process as that described for evaluation 2 was used to react the feedstock oil and then perform a compositional analysis of the resulting products to evaluate the catalytic activity following hydrothermal degradation. The evaluation results are shown in Table 2.

[Catalyst Degradation]

A value was calculated for the ratio of the amount (% by mass) of monocyclic aromatic hydrocarbons of 6 to 8 carbon number in the catalytic activity evaluation following hydrothermal degradation (evaluation 3) relative to the amount (% by mass) of monocyclic aromatic hydrocarbons of 6 to 8 carbon number in the initial reaction catalytic activity evaluation (evaluation 1 or evaluation 2) (namely, [amount (% by mass) of monocyclic aromatic hydrocarbons of 6 to 8 carbon number in evaluation 3]/[amount (% by mass) of monocyclic aromatic hydrocarbons of 6 to 8 carbon number in evaluation 1 or evaluation 2]), and this value was used to determine the degree of catalyst degradation. The results are summarized in Table 2. A larger value for this property indicates superior resistance to catalyst degradation.

TABLE 1

| | Feedstock properties | | | Analysis method |
|---|---|---|---|---|
| Density (Measurement temperature: 15° C.) | | g/cm$^3$ | 0.906 | JIS K 2249 |
| Kinematic viscosity (Measurement temperature: 30° C.) | | mm$^2$/s | 3.640 | JIS K 2283 |
| Distillation characteristics | Initial boiling point | ° C. | 175.5 | JIS K2254 |
| | 10 volume % distillation temperature | ° C. | 224.5 | |
| | 50 volume % distilintion temperature | ° C. | 274.0 | |
| | 90 volume % distilintion temperature | ° C. | 349.5 | |
| | End point temperature | ° C. | 376.0 | |
| Compositional analysis | Saturated content | volume % | 35 | JPI-5S-49 |
| | Olefin content | volume % | 8 | |
| | Total aromatic content | volume % | 57 | |
| | Monocyclic aromatic content | volume % | 23 | |
| | Bicyclic aromatic content | volume % | 25 | |
| | Triyclic and higher aromatic content | volume % | 9 | |

TABLE 2

| Granulated catalyst preparation method | | Example 1 | | Example 2 | | Example 3 | | Example 4 | |
|---|---|---|---|---|---|---|---|---|---|
| Amount of phosphorus within crystalline aluminosilicate (% by mass) | | 0.2 | | 0.7 | | 1.2 | | 0.7 | |
| Evaluation test | | Evaluation 1 | Evaluation 3 | Evaluation 1 | Evaluation 3 | Evaluation 1 | Evaluation 3 | Evaluation 1 | Evaluation 3 |
| Catalyst | | Granulated catalyst 1 | Pseudo-degraded catalyst 1 | Granulated catalyst 2 | Pseudo-degraded catalyst 2 | Granulated catalyst 3 | Pseudo-degraded catalyst 3 | Granulated catalyst 4 | Pseudo-degraded catalyst 4 |
| Products (% by mass) | Heavy fraction | 48 | 55 | 49 | 52 | 54 | 54 | 53 | 53 |
| | Monocyclic aromatic hydrocarbons of 6 to 8 carbon atoms | 43 | 31 | 38 | 34 | 26 | 27 | 32 | 29 |
| | Light naphtha | 0 | 0 | 0 | 0 | 1 | 0 | 0 | 0 |
| | Liquefied petroleum gas | 1 | 6 | 5 | 5 | 11 | 10 | 6 | 9 |
| | Cracked gas | 5 | 7 | 7 | 7 | 8 | 8 | 8 | 8 |
| | Hydrogen | 2 | 1 | 1 | 1 | 1 | 1 | 1 | 1 |
| [Amount (% by mass) of monocyclic aromatic hydrocarbons in evaluation 3]/[amount (% by mass) of monocyclic aromatic hydrocarbons in evaluation 1 or evaluation 2] | | 0.72 | | 0.91 | | 1.05 | | 0.91 | |

| | | Example 5 | | Comparative example 1 | | Comparative example 2 | |
|---|---|---|---|---|---|---|---|
| Granulated catalyst preparation method | | | | | | | |
| Amount of phosphorus within crystalline aluminosilicate (% by mass) | | 0.7 | | 2.0 | | 0 | |
| Evaluation test | | Evaluation 2 | Evaluation 3 | Evaluation 1 | Evaluation 3 | Evaluation 1 | Evaluation 3 |
| Catalyst | | Powdered catalyst 6 | Pseudo-degraded catalyst 6 | Granulated catalyst 7 | — | Granulated catalyst 8 | Pseudo-degraded catalyst 8 |
| Products (% by mass) | Heavy fraction | 50 | 52 | 60 | — | 48 | 64 |
| | Monocyclic aromatic hydrocarbons of 6 to 8 carbon atoms | 35 | 32 | 5 | — | 42 | 14 |
| | Light naphtha | 0 | 0 | 5 | — | 0 | 3 |
| | Liquefied petroleum gas | 6 | 7 | 22 | — | 2 | 12 |
| | Cracked gas | 8 | 8 | 7 | — | 6 | 6 |
| | Hydrogen | 1 | 1 | 0 | — | 2 | 1 |

TABLE 2-continued

| | | | |
|---|---|---|---|
| [Amount (% by mass) of monocyclic aromatic hydrocarbons in evaluation 3]/[amount (% by mass) of monocyclic aromatic hydrocarbons in evaluation 1 or evaluation 2] | 0.91 | — | 0.33 |

Evaluation 1 or evaluation 2: Initial reaction catalytic activity
Evaluation 3: Catalytic activity following hydrothermal degradation

[Results]

Examples 1 to 6, which employed the granulated catalysts 1 to 5 and the powdered catalyst 6 respectively, exhibited favorable initial reaction catalytic activity and favorable catalytic activity following hydrothermal degradation, and the monocyclic aromatic hydrocarbons of 6 to 8 carbon number which are objective products in the present embodiment were able to be obtained in high yield, both during the initial reaction and following hydrothermal degradation.

On the other hand, the results for Comparative Example 1 revealed that if a large amount of phosphorus is added, then the yield of monocyclic aromatic hydrocarbons of 6 to 8 carbon number decreases markedly, even during the initial reaction.

The results for Comparative Example 2 revealed that if a catalyst with no phosphorus supported thereon is used, despite the yield of monocyclic aromatic hydrocarbons of 6 to 8 carbon number is favorable during the initial reaction, the yield decreases significantly following hydrothermal degradation, and the deterioration in the catalyst is marked, making the catalyst impractical.

The invention claimed is:

1. A method for producing monocyclic aromatic hydrocarbons of 6 to 8 carbon number, the method comprising bringing a feedstock oil containing polycyclic aromatic hydrocarbons and having a 10 volume % distillation temperature of at least 140° C. and an end point temperature of not more than 400° C., or a feedstock oil containing polycyclic aromatic hydrocarbons and having a 10 volume % distillation temperature of at least 140° C. and a 90 volume % distillation temperature of not more than 360° C., into contact with a catalyst comprising a medium pore size zeolite, gallium and/or zinc, and phosphorus,
    wherein the amount of phosphorus supported on the medium pore size zeolite is within a range from 0.1 to 1.9% by mass based on the mass of the medium pore size zeolite.

2. The method according to claim 1, wherein a cracked gas oil produced in a fluid catalytic cracking is used as the feedstock oil.

3. The method according to claim 1, wherein the feedstock oil is brought into contact with the catalyst in a fluidized bed reactor.

4. The method according to claim 1, wherein the medium pore size zeolite is a pentasil-type zeolite.

5. The method according to claim 1, wherein the medium pore size zeolite is an MFI-type zeolite.

6. A method for producing monocyclic aromatic hydrocarbons of 6 to 8 carbon number, the method comprising bringing a feedstock oil containing polycyclic aromatic hydrocarbons and having a 10 volume % distillation temperature of at least 140° C. and an end point temperature of not more than 400° C., or a feedstock oil containing polycyclic aromatic hydrocarbons and having a 10 volume % distillation temperature of at least 140° C. and a 90 volume % distillation temperature of not more than 360° C., into contact with a catalyst comprising a medium pore size zeolite, gallium and/or zinc, and phosphorus,
    wherein the amount of phosphorus is within a range from 0.1 to 5.0% by mass based on the mass of the catalyst.

7. The method according to claim 6, wherein a cracked gas oil produced in a fluid catalytic cracking is used as the feedstock oil.

8. The method according to claim 6, wherein the feedstock oil is brought into contact with the catalyst in a fluidized bed reactor.

9. The method according to claim 6, wherein the medium pore size zeolite is a pentasil-type zeolite.

10. The method according to claim 6, wherein the medium pore size zeolite is an MFI-type zeolite.

* * * * *